United States Patent
Mertens et al.

(10) Patent No.: US 8,859,836 B2
(45) Date of Patent: Oct. 14, 2014

(54) HYDROCARBON CONVERSION PROCESS USING MOLECULAR SIEVE OF MFS FRAMEWORK TYPE

(75) Inventors: Machteld M. Mertens, Boortmeerbeek (BE); An Verberckmoes, Serskamp (BE); Ivy D. Johnson, Laurenceville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 50 days.

(21) Appl. No.: 13/461,223

(22) Filed: May 1, 2012

(65) Prior Publication Data

US 2012/0264987 A1    Oct. 18, 2012

Related U.S. Application Data

(62) Division of application No. 11/699,166, filed on Jan. 29, 2007, now Pat. No. 8,187,569.

(60) Provisional application No. 60/773,035, filed on Feb. 14, 2006.

(51) Int. Cl.

| | |
|---|---|
| B01J 29/70 | (2006.01) |
| C01B 39/48 | (2006.01) |
| C07C 2/12 | (2006.01) |
| C10G 49/08 | (2006.01) |
| E05B 65/08 | (2006.01) |
| E05B 63/20 | (2006.01) |

(52) U.S. Cl.
CPC . *E05B 65/08* (2013.01); *C07C 2/12* (2013.01); *C10G 49/08* (2013.01); *B01J 29/7026* (2013.01); *B01J 2231/20* (2013.01); *C10G 2400/22* (2013.01); *C01B 39/48* (2013.01); *E05B 63/20* (2013.01); *C10G 2400/20* (2013.01); *Y10S 585/906* (2013.01)
USPC ............ 585/533; 585/906; 208/111.001; 208/120.01; 208/135; 208/143; 423/701; 423/702; 423/703; 423/704; 423/705; 423/709

(58) Field of Classification Search
USPC ............ 423/700–718; 502/77; 585/533, 906; 208/111.01, 120.01, 135, 143
See application file for complete search history.

(56) References Cited

U.S. PATENT DOCUMENTS

| | | |
|---|---|---|
| 4,100,262 A | 7/1978 | Pelrine et al. |
| 4,439,409 A | 3/1984 | Puppe et al. |
| 4,721,806 A | 1/1988 | Zinnen |
| 4,826,667 A | 5/1989 | Zones et al. |
| 4,873,067 A | 10/1989 | Valyocsik et al. |
| 4,954,325 A | 9/1990 | Rubin et al. |
| 4,956,663 A | 9/1990 | Gerstch |
| 4,973,781 A | 11/1990 | Valyocsik et al. |
| 5,164,170 A | 11/1992 | Rubin |
| 5,236,575 A | 8/1993 | Bennett et al. |
| 5,250,277 A | 10/1993 | Kresge et al. |
| 5,362,697 A | 11/1994 | Fung et al. |
| 5,558,851 A | 9/1996 | Miller |
| 5,895,769 A | 4/1999 | Lai |
| 6,077,498 A | 6/2000 | Diaz Cabanas et al. |
| 6,099,820 A | 8/2000 | Miller |
| 6,936,744 B1 | 8/2005 | Cheng et al. |
| 7,816,573 B2 | 10/2010 | Lai et al. |
| 8,017,540 B2 | 9/2011 | Lai et al. |
| 2004/0030212 A1 | 2/2004 | Al-Soufi et al. |
| 2005/0013774 A1 | 1/2005 | Dakka et al. |
| 2007/0191656 A1 | 8/2007 | Lai et al. |
| 2007/0191657 A1 | 8/2007 | Lai et al. |
| 2007/0191658 A1 | 8/2007 | Lai et al. |
| 2007/0191659 A1 | 8/2007 | Lai et al. |
| 2007/0191660 A1 | 8/2007 | Johnson et al. |
| 2007/0191663 A1 | 8/2007 | Mertens et al. |
| 2010/0147741 A1 | 6/2010 | Lai et al. |

FOREIGN PATENT DOCUMENTS

| | | |
|---|---|---|
| CN | 1 296 913 | 5/2001 |
| EP | 0 174 121 | 3/1986 |
| EP | 0 284 206 | 9/1988 |
| EP | 0 293 032 | 11/1988 |
| EP | 0 999 182 | 5/2000 |
| EP | 1 105 348 | 6/2001 |
| EP | 1 249 428 | 10/2002 |
| EP | 1 061 046 | 9/2007 |
| WO | 92/12928 | 8/1992 |
| WO | 97/17290 | 5/1997 |
| WO | 03/006160 | 1/2003 |
| WO | 03/029144 | 4/2003 |
| WO | 03/093230 | 11/2003 |
| WO | 2005/118476 | 12/2005 |
| WO | 2007/094949 | 8/2007 |

OTHER PUBLICATIONS

Lok et al., "The Role of Organic Molecules in Molecular Sieve Synthesis" Zeolites, vol. 3, Oct. 1983, pp. 282-291.
Corma et al., "Synthesis and characterization of the MCM-22 zeolite", Zeolite 15: pp. 2-8, 1995.
Guray et al., "Synthesis of zeolite MCM-22 under rotating and static conditions", Microporous and Mesoporous Materials 31 (1999), pp. 241-251.
Inagaki et al., "Textural and Catalytic Properties of MCM-22 Zeolite Crystallized by the Vapor-Phase Transport Method", Bull. Chem. Soc. Jpn., 77, (2004), pp. 1249-1254.
Kim et al., "Synthesis of zeolites by water-organic vapor-phase transport", Microporous Materials, 1 (1993), pp. 191-200.

(Continued)

*Primary Examiner* — David M Brunsman
(74) *Attorney, Agent, or Firm* — Darryl M. Tyus (57) ABSTRACT

A crystalline molecular sieve of MFS framework type manufactured by the method disclosed herein. A hydrocarbon conversion process using the crystalline molecular sieve is disclosed.

13 Claims, 8 Drawing Sheets

(56) References Cited

OTHER PUBLICATIONS

Marques et al., "Static crystallization of zeolites MCM-22 and MCM-49", Microporous and Mesoporous Materials 32 (1999), pp. 131-145.

Matsukata et al., "Synthesis of zeolites under vapor atmosphere, Effect of synthetic conditions on zeolite structure", Microporous Materials, 1 (1993) pp. 219-222.

Ravishankar et al., "Characterization and catalytic properties of zeolite MCM 22", Microporous Materials 4 (1995), pp. 83-93.

Xu et al., "A Novel Method for the Preparation of Zeolite ZSM-5", J. Chem. Soc., Chem. Commun., (1990), pp. 755-756.

Stiles et al., *Catalyst Manufacture*, Second Edition, Marcel Dekker, Inc., New York (1995).

Szostak, *Molecular Sieves—Principles of Synthesis and Identification*, Second Edition, Blackie Academic & Professional, London (1998).

Figure 1
SEM Reference example

Figure 2
SEM example 1

Figure 3
SEM example 2

Figure 4
SEM example 3

Figure 5
SEM example 4

Figure 6
SEM example 5

HYDROCARBON CONVERSION PROCESS USING MOLECULAR SIEVE OF MFS FRAMEWORK TYPE

CROSS-REFERENCE TO RELATED APPLICATIONS

This application is a divisional of U.S. application Ser. No. 11/699,166, filed Jan. 29, 2007, now U.S. Pat. No. 8,187,569, which claims the benefits of and priority to U.S. Provisional Application No. 60/773,035, filed Feb. 14, 2006, the disclosures of which are incorporated herein by reference in their entireties.

FIELD

This invention relates to a molecular sieve of MFS framework type, its method of manufacture, and to its use in catalytic conversion of organic compounds.

BACKGROUND OF THE INVENTION

Molecular sieves of the MFS framework type, and in particular ZSM-57, are useful catalyst components for a variety of conversion processes, such as hydrocarbon cracking, dehydrogenation, oligomerization, isomerization, disproportionation, and alkylation as well as the formation of hydrocarbons from oxygen-containing compounds such as alcohols and ethers.

The composition, properties and preparation of ZSM-57 are disclosed in European Patent No. 174,121, and U.S. Pat. Nos. 4,873,067 and 4,973,781, the entire disclosures of these documents being incorporated by reference herein. ZSM-57 is a zeolite with a typical molar ratio of $YO_2:X_2O_3$ of at least 4, wherein Y represents silicon and/or germanium and X represents aluminum, and/or boron, and/or chromium, and/or iron, and/or gallium. Preferably, there are from greater than 8 to about 200 moles of $YO_2$ per mole of $X_2O_3$. Preferably, $YO_2$ is silica and $X_2O_3$ is alumina.

ZSM-57 may be prepared as described in European Patent No. 174,121 from a synthesis mixture containing sources of alkali metal ions, an oxide of silicon, an oxide of aluminum, water and an organic directing agent which is a salt of N,N,N,N',N',N'-hexaethylpentane diammonium (HEPD, also known as hexaethyl-Diquat-5), and maintaining said mixture under crystallization conditions until the required zeolite is formed. The synthesis mixture has a composition within the following ranges: $SiO_2:Al_2O_3$ of 20 to 200:1, preferably 40 to 100:1; $H_2O:SiO_2$ of 10 to 200:1, preferably of 20 to 50:1; $OH^-:SiO_2$ of 0 to 3:1, preferably 0.1 to 0.5:1; $Z:SiO_2$ of 0 to 3:1, preferably of 0.1 to 2:1, where Z is an alkali metal cation; $R:SiO_2$ of 0.01 to 2:1, preferably of 0.1:1, where R is HEPD, preferably its dibromide salt. Crystallization of zeolite ZSM-57 may be carried out under either static or stirred conditions. A useful range of temperatures for crystallization is from 80° C. to 350° C. for a time of 12 hours to 200 days. Thereafter, the crystals are separated from the liquid and recovered. The synthesis of the zeolite crystals is said to be facilitated by the presence of at least 0.01 wt. percent, preferably 0.10 wt. %, and still more preferably 1 wt. %, seed crystals (based on total weight) of crystalline product.

U.S. Patent Application No. 20050013774 A1 discloses a process for the manufacture of a crystalline molecular sieve of the MFS framework type, which comprises hydrothermal treatment of a synthesis mixture containing sources of alkali metal ions, of aluminum, and of silicon, water, an N,N,N,N',N',N'-hexaethylpentane diammonium salt (HEPD), hereinafter $R_1$, and $R_2$, an amine of formula $NR^1R^2R^3$ or a quaternary ammonium compound of formula $R^1R^2R^3R^4NX$, wherein $R^1$, $R^2$, $R^3$, or $R^4$, which may be identical or different, each independently represent a hydrogen atom, a linear alkyl group having from 1 to 8 carbon atoms, a branched alkyl group having from 3 to 8 carbon atoms, or a cycloalkyl group having 5 or 6 carbon atoms, at least one of $R^1$, $R^2$, $R^3$, and if present $R^4$, being other than hydrogen, and X represents an anion.

U.S. Pat. No. 4,873,067 further illustrates the preparation of boron, chromium, iron and/or gallium-containing zeolite ZSM-57 by a method comprising preparing a mixture containing sources of alkali metal ions, an oxide of silicon, an oxide of aluminum, a source of boron, and/or chromium, and/or iron and/or gallium, water and HEPD, and maintaining said mixture under crystallization conditions until the required zeolite is formed.

Colloidal seeds have proved effective in controlling the particle size of the product, avoiding the need for an organic directing agent, accelerating synthesis, and improving the proportion of product that is of the intended framework type. European Patent No. 1105348 provides a colloidal suspension of a LEV framework type crystalline molecular sieve and a method for preparing a colloidal suspension of LEV by synthesizing a LEV framework type crystalline molecular sieve by treatment of an appropriate synthesis mixture, separating the product from the synthesis mixture, washing the product, and recovering the resulting wash liquid.

The ZSM-57 material that is commercially available, however, is expensive and time consuming for manufacturing. There is therefore a need for an improved high throughput process for manufacturing the ZSM-57 material. We have now found that the throughput of the process for preparing the crystalline molecular sieves of the MFS framework type is improved by lowering the alkali and the water content of the synthesis mixture and/or by increasing the crystallization temperature.

SUMMARY OF THE INVENTION

In one embodiment, this invention relates to a method of making a crystalline molecular sieve of MFS framework type, the method comprising the steps of:
(a) providing a mixture comprising at least one source of ions of tetravalent element (Y), at least one source of ions of trivalent element (X), at least one hydroxide source ($OH^-$), at least one structure-directing-agent (R), at least one seed source (Seed), and water ($H_2O$), said mixture having the following mole composition (expressed in term of oxide):

$YO_2:(n)X_2O_3:(x)OH^-:(y)R:(z)H_2O+(m)Seed$ wherein m is in the range of from about 10 wtppm to about 2 wt. %, preferably from about 10 to 2000 wtppm, and more preferably from about 1000 to 2000 wtppm (based on total weight of the synthesis mixture); n is in the range of from about 0.005 to 0.05, preferably from about 0.01 to 0.05; x is in the range of from about 0.01 to about 0.3, preferably from about 0.01 to 0.2; y is in the range of from about 0.03 to about 2, preferably from about 0.03 to 0.2, more preferably from about 0.035 to 0.2, even more preferably from about 0.04 to about 0.2; and z is in the range of from about 3 to about 30, preferably from about 3 to 15, more preferably from about 3 to 10, optionally from about 8 to 10; and
(b) treating the mixture under crystallization conditions to form the crystalline molecular sieve of MFS framework type, wherein the structure-directing-agent R containing N,N,N, N',N',N'-hexaethylpentane diammonium salt ($R_1$), the crystallization conditions comprise a temperature in the range of from about 150° C. to about 250° C., and crystallization time less than 100 hr, and wherein the weight hourly throughput is at least 0.001 $hr^{-1}$.

In another embodiment, this invention relates to a process of manufacturing crystalline molecular sieve of MFS framework type, the method comprising the steps of:
(a) providing a mixture comprising at least one silicon source ($SiO_2$), at least one aluminum source ($Al_2O_3$), at least one hydroxide source ($OH^-$), at least one structure-directing-agent (R), LEV seeds, and water ($H_2O$), said mixture having the following mole composition:

$SiO_2:(n)Al_2O_3:(x)OH^-:(y)R:(z)H_2O+(m)Seed$ wherein m is in the range of from about 10 wtppm to about 2 wt. %, preferably from about 10 to 2000 wtppm, and more preferably from about 1000 to 2000 wtppm (based on total weight of the synthesis mixture); n is in the range of from about 0.005 to 0.05, preferably from about 0.01 to 0.05; x is in the range of from about 0.01 to about 0.3, preferably from about 0.01 to 0.2; y is in the range of from about 0.03 to about 2, preferably from about 0.03 to 0.2, more preferably from about 0.035 to 0.2, even more preferably from about 0.04 to about 0.2; and z is in the range of from about 3 to about 30, preferably from about 3 to 15, more preferably from about 3 to 10, optionally from about 8 to 10;
(b) treating the mixture under crystallization conditions to form a product containing crystalline molecular sieve of MFS framework type; and
(c) recovering the crystalline molecular sieve of MFS framework type from the product,
wherein the structure-directing-agent R comprises N,N,N,N', N',N'-hexaethylpentane diammonium salt ($R_1$), the crystallization conditions comprise a temperature in the range of from about 150° C. to about 250° C., and crystallization time less than 100 hr, and wherein the weight hourly throughput is at least 0.001 $hr^{-1}$.

In yet another embodiment, this invention relates to a crystalline molecular sieve of MFS framework type manufactured by the process comprising the steps of:
(a) providing a mixture comprising at least one silicon source ($SiO_2$), at least one aluminum source ($Al_2O_3$), at least one hydroxide source ($OH^-$), at least one structure-directing-agent (R), LEV seeds, and water ($H_2O$), said mixture having the following mole composition:

$SiO_2:(n)Al_2O_3:(x)OH^-:(y)R:(z)H_2O+(m)Seed$ wherein m is in the range of from about 10 wtppm to about 2 wt. %, preferably from about 10 to 2000 wtppm, and more preferably from about 1000 to 2000 wtppm (based on total weight of the synthesis mixture); n is in the range of from about 0.005 to 0.05, preferably from about 0.01 to 0.05; x is in the range of from about 0.01 to about 0.3, preferably from about 0.01 to 0.2; y is in the range of from about 0.03 to about 2, preferably from about 0.03 to 0.2, more preferably from about 0.035 to 0.2, even more preferably from about 0.04 to about 0.2; and z is in the range of from about 3 to about 30, preferably from about 3 to 15, more preferably from about 3 to 10, optionally from about 8 to 10;
(b) treating the mixture under crystallization conditions to form the a product containing crystalline molecular sieve of MFS framework type; and
(c) recovering the crystalline molecular sieve of MFS framework type from the product,
wherein the structure-directing-agent R comprises N,N,N,N', N',N'-hexaethylpentane diammonium salt ($R_1$), the crystallization conditions comprise a temperature in the range of from about 150° C. to about 250° C., and crystallization time less than 100 hr, and wherein the weight hourly throughput is at least 0.001 $hr^{-1}$.

In an embodiment, this invention relates to a process for hydrocarbon conversion comprising the step of contacting the hydrocarbon with a crystalline molecular sieve of MFS framework type manufactured by the method and/or process disclosed in the preceding paragraphs.

These and other facets of the present invention shall become apparent from the following detailed description, figures, and appended claims.

DETAILED DESCRIPTION OF THE INVENTION

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," eds. Ch. Baerlocher, W. H. Meier, and D. H. Olson, Elsevier, Fifth Edition, 2001, which is hereby incorporated by reference.

Synthetic zeolites are often prepared from aqueous synthesis mixtures comprising sources of appropriate oxides. Organic directing agents may also be included in the synthesis mixture for the purpose of influencing the production of a zeolite having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

The invention more especially provides a high throughput process for the manufacture of a crystalline molecular sieve of the MFS framework type which comprises subjecting to hydrothermal treatment a synthesis mixture having a composition within the molar ranges of:

| | |
|---|---|
| 20 to 200 | YO$_2$:X$_2$O$_3$ |
| 3 to 30 | H$_2$O:YO$_2$ |
| 0.01 to 0.3 | OH$^-$:YO$_2$ |
| 0.01 to 0.3 | M$^+$:YO$_2$ |
| 0.03 to 2 | R:YO$_2$ | wherein M$^+$ represents an alkali metal ion, R represents directing agent, e.g., R$_1$ (HEPD) or R$_1$ with additional directing agent R$_2$. When both R$_1$ and R$_2$ are present in the synthesis mixture, the synthesis mixture preferably has a composition within the molar ranges of:

| | |
|---|---|
| 20 to 200 | YO$_2$:X$_2$O$_3$ |
| 3 to 30 | H$_2$O:YO$_2$ |
| 0.01 to 0.3 | OH$^-$:YO$_2$ |
| 0.01 to 0.3 | M$^+$:YO$_2$ |
| 0.015 to 2 | R$_1$:YO$_2$ |
| 0.015 to 2 | R$_2$:YO$_2$ |
| 0.03 to 2 | (R$_1$ + R$_2$):YO$_2$ |

Preferred molar ranges are:

| | |
|---|---|
| 40 to 100 | YO$_2$:X$_2$O$_3$ |
| 3 to 15 | H$_2$O:YO$_2$ |
| 0.05 to 0.2 | OH$^-$:YO$_2$ |
| 0.05 to 0.2 | M$^+$:YO$_2$ |
| 0.015 to 0.3 | R$_1$:YO$_2$ |
| 0.015 to 0.3 | R$_2$:YO$_2$ |

It will be understood by a person skilled in the art that the synthesis mixture having a composition within the molar ranges as discussed above means that the synthesis mixture is the product of mixing, adding, reacting, or by any means of providing such a mixture, wherein such product has a composition within the molar ranges as discussed above. The product of mixing, adding, reacting, or by any means of providing such a mixture may or may not contain individual ingredients when the product was prepared. The product of mixing, adding, reacting, or by any means of providing such a mixture, may even contain reaction product of individual ingredients when the product was prepared by mixing, adding, reacting, or by any means of providing such a mixture.

It will be understood by a person skilled in the art that the crystalline molecular sieve manufactured by the process or method of this invention may contain impurities, such as amorphous materials; unit cells having non-MFS framework topologies (e.g., MFI, MTW); and/or other impurities (e.g., heavy metals and/or organic hydrocarbons). The crystalline molecular sieve manufactured by the process or method of this invention is preferably substantially free of non-MFS material. The term "substantially free of non-MFS material" used herein means the crystalline molecular sieve contains minor proportion (less than 50 wt. %), preferably less than 20 wt. %, more preferably less than 10 wt. %, even more preferably less than 5 wt. %, and most preferably less than 1 wt. %, of such non-MFS materials based on the combination weight of non-MFS materials and the molecular sieve(s) of MFS framework type. The term "non-MFS material" used herein means any material does not contain crystalline molecular sieve of MFS framework type. Examples of such non-MFS material are amorphous material, ZSM-5 (MFI framework type), mordenite (MOR framework type), Y and X zeolites (FAU framework type), and MCM-22 (MWW framework type). The non-MFS material may co-crystallize with the MFS material or mix with the MFS material.

The sources of the various elements required in the final product may be any of those in commercial use or described in the literature, as may the method of preparation of the synthesis mixture.

In the present synthesis method, the source of ions of tetravalent element Y preferably comprises solid YO$_2$, preferably about 30 wt. % solid YO$_2$ in order to obtain the crystal product of this invention. Examples of tetravalent element are silicon, germanium, and tin. When YO$_2$ is silica, the use of a silica source containing preferably about 30 wt. % solid silica, e.g., silica sold by Degussa under the trade names Aerosil or Ultrasil (a precipitated, spray dried silica containing about 90 wt. % silica), an aqueous colloidal suspension of silica, for example one sold by Grace Davison under the trade name Ludox, or HiSil (a precipitated hydrated SiO$_2$ containing about 87 wt. % silica, about 6 wt. % free H2O and about 4.5 wt. % bound H$_2$O of hydration and having a particle size of about 0.02 micro) favors crystal formation from the above mixture. Preferably, therefore, the YO$_2$, e.g., silica, source contains about 30 wt. % solid YO$_2$, e.g., silica, and more preferably about 40 wt. % solid YO$_2$, e.g., silica. The source of silicon may also be a silicate, e.g., an alkali metal silicate, or a tetraalkyl orthosilicate.

The source of ions of trivalent element X, e.g., aluminum, boron, gallium, and iron, is preferably aluminum sulphate or hydrated alumina Other aluminum sources include, for example, other water-soluble aluminum salts, sodium aluminate, or an alkoxide, e.g., aluminum isopropoxide, or aluminum metal, e.g., in the form of chips.

The alkali metal is advantageously potassium or sodium, the sodium source advantageously being sodium hydroxide or sodium aluminate.

Directing Agent

The directing agent used in this invention comprises an N,N,N,N',N',N'-hexaethylpentane diammonium salt (HEPD), hereinafter R$_1$, optionally with one or another directing agent, R$_2$, were R$_2$ comprises an amine of formula NR$^1$R$^2$R$^3$ or a quaternary ammonium compound of formula R$^1$R$^2$R$^3$R$^4$NA, wherein R$^1$, R$^2$, R$^3$, or R$^4$, which may be identical or different, each independently represent a hydrogen atom, a linear alkyl group having from 1 to 8 carbon atoms, a branched alkyl group having from 3 to 8 carbon atoms, or a cycloalkyl group having 5 or 6 carbon atoms, at least one of R$^1$, R$^2$, R$^3$, and if present R$^4$, being other than hydrogen, and A represents an anion. Mixtures of two or more compounds R$_1$ may be used. Mixtures of two or more compounds R$_2$ may also be used. These may be mixtures of two or more amines, or of two or more quaternary compounds, or of one or more amines and one or more quaternary compounds.

As amine for use as a second organic molecule there may be mentioned, for example, mono, di- and tri-methylamine, mono-, di- and triethylamine, mono-, di- and tri propylamines, mono-, di- and trihexylamines, mono-, di- and tri-heptylamines, mono-, di- and trioctylamines, cyclopentylamine and cyclohexylamine Advantageously, the amine is a triamine, i.e., none of R$^1$, R$^2$, and R$^3$ represents hydrogen. Preferably, the amine of formula NR$^1$R$^2$R$^3$ is selected from trimethylamine, triethylamine and a tripropylamine; most preferably it is triethylamine. Advantageously, the quaternary ammonium compound corresponds to one of the above amines, and is preferably a tetralkylammonium compound, preferably a tetramethyl-, tetraethyl-, or tetrapropyl-ammonium compound, a tetra ethylammonium compound being most preferred. As examples of the anion there may be mentioned halide, especially chloride or bromide, and hydroxide. Mixtures of these compounds may be used, as indicated above.

LEV Seed

The synthesis may be aided by seeds from a previous synthesis, the seeds being advantageously colloidal or near-colloidal. Seeds of a different framework type, especially LEV, may be used. The preparation of colloidal LEV seeds is described in International application WO 00/06494. Seeds are advantageously present in a proportion of from 0.0001 wt. % (10 weight part per million or "wtppm") to 2 wt. %, preferably 0.001 wt. % to 1 wt. %, more preferably 0.01 wt. % to 0.5 wt. %, by weight, based on the total weight of synthesis mixture. For certain synthesis mixtures, a pure MFS framework type material is more readily obtained with seeding.

As used herein, the term "colloidal", when used of a suspension, refers to one containing discrete finely divided particles dispersed in a continuous liquid phase and preferably refers to a suspension that is stable, in the sense that no visible separation occurs or sediment forms, in a period sufficient for the use intended, advantageously for at least 10, more advantageously at least 20, preferably at least 100, and more preferably at least 500, hours at ambient temperature (23° C.). The maximum size of the particles for the suspension to remain stable (peptized) will depend to some extent on their shape, and on the nature and pH of the continuous medium, as well as on the period during which the suspension must remain usable. In general, the maximum dimension will be 500, advantageously 400, preferably 300, more preferably 200, and most preferably 100, nm. The particles may be spherical, or of other shapes. Where particles are other than spherical, the dimension referred to is their smallest dimension.

As indicated above, the colloidal seeds have utility in the manufacture of a variety of crystalline molecular sieves by incorporating the seeds as a component of a synthesis mixture. They are advantageously incorporated in the synthesis mixture in the form of a suspension, advantageously in an aqueous medium, preferably water, or another liquid component of the synthesis mixture. Less preferably they may be added in dry, but not calcined, form. It is believed that calcination significantly reduces the activity of small crystallites to act as seeds; similarly any other treatment that reduces the seeding activity of materials should be avoided.

Crystallization Conditions

In general, the treatment of the synthesis mixture to yield the desired crystalline molecular sieve, usually termed hydrothermal treatment is conveniently carried out under autogenous pressure, for example in an autoclave, which may, if desired, be PTFE-lined. The treatment may, for example, be carried out at a temperature within the range of from 50, advantageously from 90, especially 120, preferably 150, to 250° C. The treatment may, for example, be carried out for a period within the range of from 1 to less than 100 hours, preferably up to 72 hours. The procedure may include an ageing period, either at room temperature or, preferably, at a moderately elevated temperature, before the hydrothermal treatment at more elevated temperature. The latter may include a period of gradual or stepwise variation in temperature.

The hydrothermal treatment may be carried out under the usual molecular sieve synthesis conditions. Advantageously used are temperatures within the range of from 100° C. to 250° C., preferably from 150° C. to 200° C., and more preferably from 160° C. to 180° C. Temperature may be increased, gradually or stepwise, during treatment. Advantageously, a time within the range of from 1 to less than 100 hours, preferably from 10 to less than 72 hours, and conveniently from 20 to 48 hours, is employed, lower temperatures corresponding to longer times.

For certain applications, the treatment is carried out with any type of agitation, e.g., stirring or rotating the vessel about a horizontal axis (tumbling). For other applications, static hydrothermal treatment is preferred. If desired, the synthesis mixture may be stirred or tumbled during an initial part of the heating stage, for example, from room temperature to an elevated, e.g., the final treatment, temperature, and be static for the remainder. Agitation generally produces a product with a smaller particle size and a narrower particle size distribution than static hydrothermal treatment.

It has been found that for certain synthesis mixture compositions, a pure MFS framework type material is more readily obtained when synthesis is carried out with agitation. For a composition that gives pure material whether synthesis is carried out with or without agitation, crystal size is normally greater if the synthesis is carried out without agitation.

The procedure may include an ageing period, either at room temperature or at a moderately elevated temperature, lower than that used for the hydrothermal treatment.

The term "throughput" used herein means the amount of crystalline molecular sieve produced per unit time (hour) and per unit volume of the synthesis gel (volume hourly throughput) or per unit weight of the synthesis gel (weight hourly throughput). The higher the throughput, the more crystalline molecular sieve produced per unit volume of the reactor and per unit amount of time. Therefore, for the same amount of the crystalline molecular sieve synthesized, the higher the throughput, generally the smaller the reactor (autoclave) needed or the shorter the time required for each synthesis. The volume hourly throughput for a synthesis may be calculated by dividing the volume of the molecular sieve produced (after drying at 120° C. for 24 hours) with the volume of the synthesis gel and the total time required for the crystallization as follows:

$$\text{volume hourly throughput} = \frac{\text{volume of the molecular sieve produced (dried at 120° C. for 24 hours)}}{(\text{volume of the synthesis gel}) \times (\text{time required for the crystallization})}$$

The weight hourly throughput for a synthesis may be calculated by dividing the weight of the molecular sieve produced (after drying at 120° C. for 24 hours) with the weight of the synthesis gel and the total time required for the crystallization as follows:

$$\text{weight hourly throughput} = \frac{\text{weight of the molecular sieve produced (dried at 120° C. for 24 hours)}}{(\text{weight of the synthesis gel}) \times (\text{time required for the crystallization})}$$

In one aspect of this invention, the weight hourly throughput for this invention is at least 0.001 $hr^{-1}$, preferably at least 0.002 $hr^{-1}$, more preferably at least 0.004 $hr^{-1}$, and most preferably at least 0.008 $hr^{-1}$.

The weight hourly throughput of a synthesis may be adjusted by changing solid-content, amount of seed used in the synthesis gel, crystallization temperature, time for crystallization, and/or any combination thereof. The weight hourly throughput and these parameters mentioned above are interrelated. Changing one parameter may affect other parameters. For example, by increasing weight hourly throughput of a synthesis under certain crystallization conditions, e.g., crystallization temperature and time, the solid-content and/or the amount of seed crystal may have to increase.

One factor affecting the synthesis of a crystalline molecular sieve is the solid-content in a synthesis mixture. The term "solid-content" used herein means the weight percentage of both trivalent and tetravalent elements (calculated as oxides) in the synthesis mixture. It can be measured by dividing the weight of both trivalent and tetravalent oxides in the synthesis mixture by the total weight of the synthesis mixture as follows:

$$\text{solid-content} = \frac{\text{the weight of the oxides in the synthesis mixture}}{\text{total weight of the synthesis mixture}}$$

The term "high solid" used herein means that the solid-content of a synthesis mixture is at least 12 wt. %, preferably at least 15 wt. %, more preferably at least 18 wt. %, yet more preferably at least 20 wt. %, and most preferably at least 30 wt. %.

Another factor affecting the synthesis of a crystalline molecular sieve is the amount of hydroxide present (e.g., alkali content), which is represented by the molar ratio of the alkali oxides over silica. We believe that the higher the solid-content, the lower the hydroxide needed in the synthesis gel to achieve high crystallinity of the ZSM-57 product.

We surprisingly found the combination of high solid-content and low alkali content greatly improves the throughput of the ZSM-57 synthesis. As demonstrated in the examples following, the weight hourly throughput increases from about 200% to about 600% under similar content of seeds and crystallization temperature.

Another factor affecting the synthesis of a crystalline molecular sieve is the temperature. High temperature, e.g., greater than 200° C., may damage the directing agent in the synthesis mixture. To perform crystallization at high temperature, more directing agent may be needed since some of the directing agent might be damaged by the caustic reactant(s) in the synthesis mixture at the high temperature. Generally, the higher the temperature, the faster the crystallization rate. However, higher temperature may damage the expensive directing agent, which in fact slows the rate of the crystallization process. The term "high temperature" as used herein means the crystallization temperature ranges from 160 to 250° C. for the synthesis of a molecular sieve having a structure of MFS.

The synthesis mixture may contain seed crystal. It is well known that seeding a molecular sieve synthesis mixture frequently has beneficial effects, for example in controlling the particle size of the product, avoiding the need for an organic directing agent, accelerating synthesis, and improving the proportion of product that is of the intended framework type. In one embodiment of this invention, synthesis of the crystalline molecular sieve is facilitated by the presence of at least 0.001 wt. % seed crystals (based on total weight of the synthesis mixture).

We surprisingly found the additional seeds and/or higher crystallization temperature in combination with high solid-content and low alkali content further improves the throughput of the ZSM-57 synthesis. As demonstrated in the examples follows, the weight hourly throughput further increases from about 600% to about 1200% under similar solid-content and alkali content conditions.

Hydrocarbon Conversion Using ZSM-57 Material

The direct product of the synthesis described above may be calcined, cation-exchanged, and otherwise treated as is known in the art. Alkali metal cations in the as-prepared or calcined form may be removed, for example by treatment with concentrated acids, e.g., HCl, or with a fugitive base, e.g., an ammonium compound, to provide the material in its hydrogen form.

The products of the invention, if required after cation exchange and/or calcining, have utility as catalyst precursors, catalysts, and separation and absorption media. They are especially useful in numerous organic, e.g., hydrocarbon, compound conversions, separations and absorptions. They may be used alone, or in admixture with other molecular sieves, in particulate form, supported or unsupported, or in the form of a supported layer. Hydrocarbon conversions include, for example, cracking, reforming, hydrofining, aromatization, oligomerization (e.g., di- and trimerization, especially of olefins having 3 to 6 carbon atoms, more especially butene trimerization), isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons.

EXAMPLES

The following numbered examples, in which all parts percentages are by weight unless otherwise indicated, illustrate the invention. Percentage yields are based on the total weight of synthesis mixture.

The N,N,N,N',N',N'-hexaethylpentane diammonium dibromide (HEPD) was prepared according to the following procedure:
1 mole of 1,5-dibromopentane and 2 moles of triethylamine were dissolved in ethanol and refluxed overnight. The resulting solution was concentrated and finally evaporated to dryness under vacuum at 35° C. The white product was recrystallized from ether and identified as HEPD (hereinafter $R_1$).

The LEV seeds sample was prepared according to the disclosure in International application WO 00/06494.

The SEM images were obtained on a JEOL JSM-6340F Field Emission Scanning Electron Microscope (SEM), using a magnification at a voltage of 2 keV.

The XRD diffraction patterns were recorded on a Stoe Stadi P Diffractometer in transmission mode, using Cu K-α radiation.

Reference Example

A synthesis mixture was prepared containing the following ingredients: a sodium aluminate solution (12.34 wt. % NaOH and 3.06 wt. % Al(OH)$_3$ in water, Alcoa Corporation, Pittsburgh, Pa., USA), a 25 wt. % solution of N,N,N,N',N',N'-hexaethylpentane di-ammonium dibromide, a 50 wt. % solution of tetraethyl ammonium bromide in water (hereinafter $R_2$), silica (Ultrasil VN 35P, 92.4 wt. % of SiO$_2$) and a 1 wt. % NaOH solution in water. To 21.2 parts of distilled water were added 0.49 parts of the NaOH solution. To this solution were added 0.12 parts of the sodium aluminate solution while stirring. This solution was stirred for 5 minutes before 0.45 parts of solution $R_1$ were added. After 5 minutes of additional stirring, 0.22 parts of solution $R_2$ were added, followed by 0.2 parts of a seeding slurry containing 5 wt. % of LEV seeds.

After 5 minutes of mixing, 2.54 parts of the Ultrasil were added. The synthesis mixture, having the following molar composition:

$$0.148Na_2O:0.018Al_2O_3:0.0246R_1:0.0246R_2:SiO_2:$$
$$28H_2O+400 \text{ wtppm of LEV seeds}$$

was stirred an additional 10 minutes before transferring to an autoclave and heated to 160° C. with a ramp rate of 25° C./hr, while stirring at 100 rotation per minute ("rpm"). The crystallization was continued for 120 hrs at 160° C.

Figure 1:
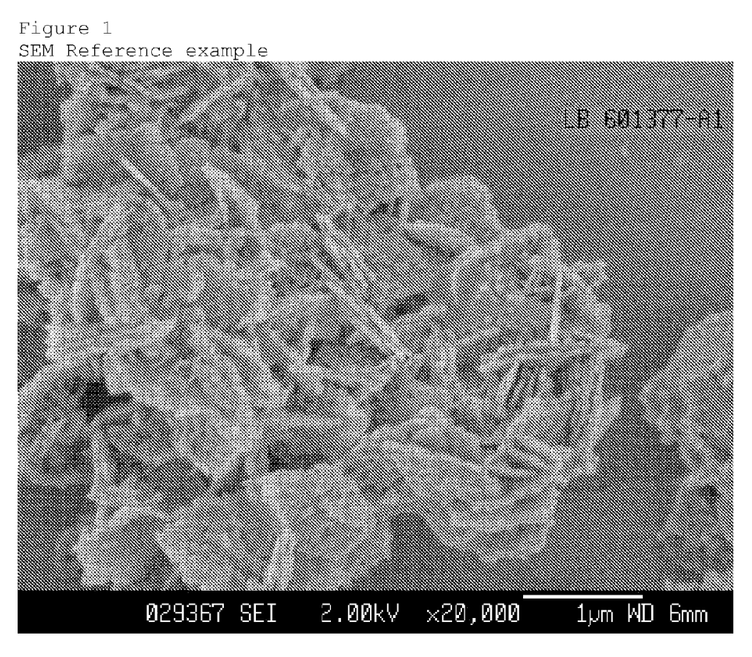
FIG. 1 is the Scan Electronic Microscopy of the dried as-synthesized solid product of the Reference Example.

After crystallization a solid product was recovered from the crystallization mixture, washed, and dried at 120° C. The yield of the crystallization was 9.3 wt. %. The SEM of the dried solid product showed plate morphology (FIG. 1). XRD analysis of the dried solid product showed it to be ZSM-57, a zeolite of the MFS framework type. An elemental analysis of the dried solid product showed a $Si/Al_2$ ratio of 43.6. The solid-content of the synthesis mixture was about 10.5 wt. %. The weight hourly throughput was 0.0008 $hr^{-1}$.

Example 1

A synthesis mixture was prepared by the procedure and raw materials used as the reference example, but with the following molar composition:

$$0.13Na_2O:0.018Al_2O_3: 0.0246R_1:0.0246R_2:SiO_2:$$
$$18H_2O+400 \text{ wtppm of LEV seeds}$$

Figure 2:
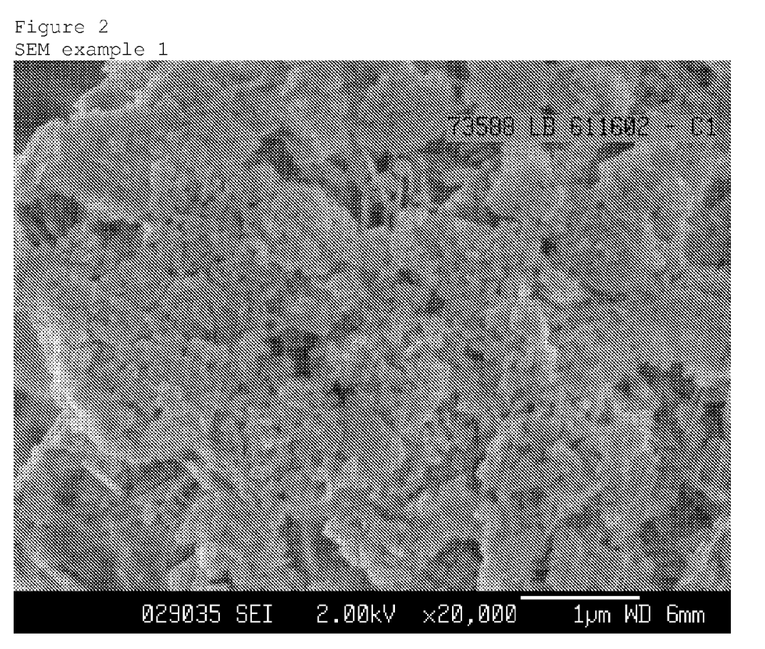
FIG. 2 is the Scan Electronic Microscopy of the dried as-synthesized solid product of Example 1.

This mixture was transferred to an autoclave and heated to 160° C. with a ramp rate of 25° C./hr, while stirring at 100 rpm. The crystallization was continued for 72 hrs at 160° C. After crystallization a solid product was recovered from the crystallization mixture, washed, and dried at 120° C. The SEM of the dried solid product showed plate morphology (FIG. 2). XRD analysis of the dried solid product showed it to be ZSM-57. The yield of the crystallization was 12.1 wt. %. Elemental analysis of the dried solid product showed a $Si/Al_2$ ratio of 42.6. The solid-content of the synthesis mixture was about 15.1 wt. %. The weight hourly throughput was 0.0017 $hr^{-1}$. The weight hourly throughput increased by about 220% in comparison with the reference example.

Comparative Example 2A

A synthesis mixture was prepared by the procedure and raw materials used as the reference example, but with the following molar composition:

$$0.12Na_2O:0.018Al_2O_3:0.0246R_1:0.0246R_2:SiO_2:$$
$$13H_2O+400 \text{ wtppm of LEV seeds}$$

This mixture was transferred to an autoclave and heated to 160° C. with a ramp rate of 25° C./hr, while stirring at 100 rpm. The crystallization was continued for 72 hrs at 160° C. After crystallization a solid product was recovered from the crystallization mixture, washed, and dried at 120° C. XRD analysis of the dried material showed it to be some ZSM-57 contaminated with mordenite. The yield of the crystallization including both ZSM-57 and mordenite was 17 wt. %. The solid-content of the synthesis mixture was about 19.4 wt. %. The weight hourly throughput was 0.0024 $hr^{-1}$. The weight hourly throughput increased by about 300% in comparison with the reference example.

Example 2

A synthesis mixture was prepared by the procedure and raw materials used as the reference example, but with the following molar composition:

$$0.11Na_2O:0.018Al_2O_3:0.0246R_1: 0.0246R_2:SiO_2:$$
$$13H_2O+400 \text{ wtppm of LEV seeds}$$

Figure 3:
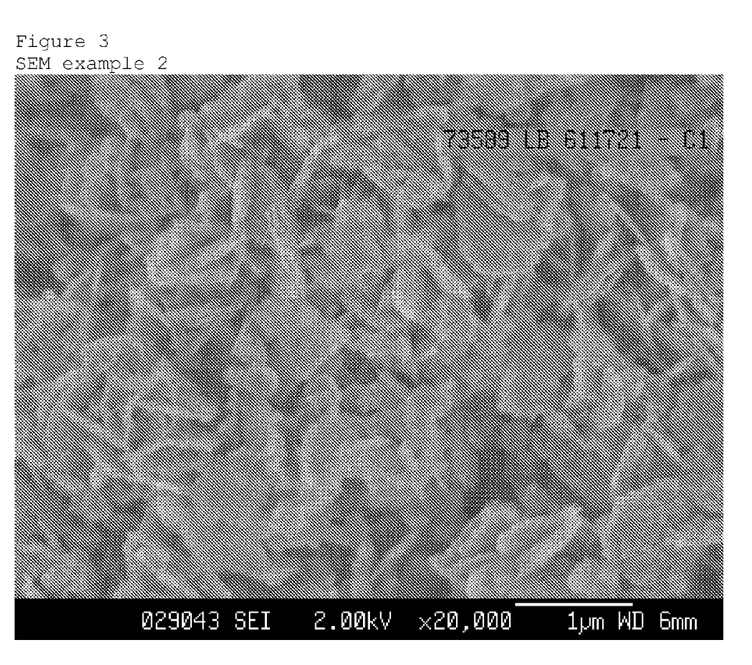
FIG. 3 is the Scan Electronic Microscopy of the dried as-synthesized solid product of Example 2.

This mixture was transferred to an autoclave and heated to 160° C. with a ramp rate of 25° C./hr, while stirring at 100 rpm. The crystallization was continued for 72 hrs at 160° C. After crystallization a solid product was recovered from the crystallization mixture, washed, and dried at 120° C. The SEM of the dried solid product showed plate morphology (FIG. 3). XRD analysis of the dried solid product showed it to be ZSM-57. The yield of the crystallization was 17.4 wt. %. Elemental analysis of the dried solid product showed a $Si/Al_2$ ratio of 45.9. The solid-content of the synthesis mixture was about 19.4 wt. %. The weight hourly throughput was 0.0024 $hr^{-1}$. The weight hourly throughput increased by about 310% in comparison with the reference example.

Example 3

A synthesis mixture was prepared by the procedure and raw materials used as the reference example, but with the following molar composition:

$$0.11Na_2O:0.018Al_2O_3:0.0246R_1:0.0246R_2:SiO_2:$$
$$10H_2O+1500 \text{ wtppm of LEV seeds}$$

Figure 4:
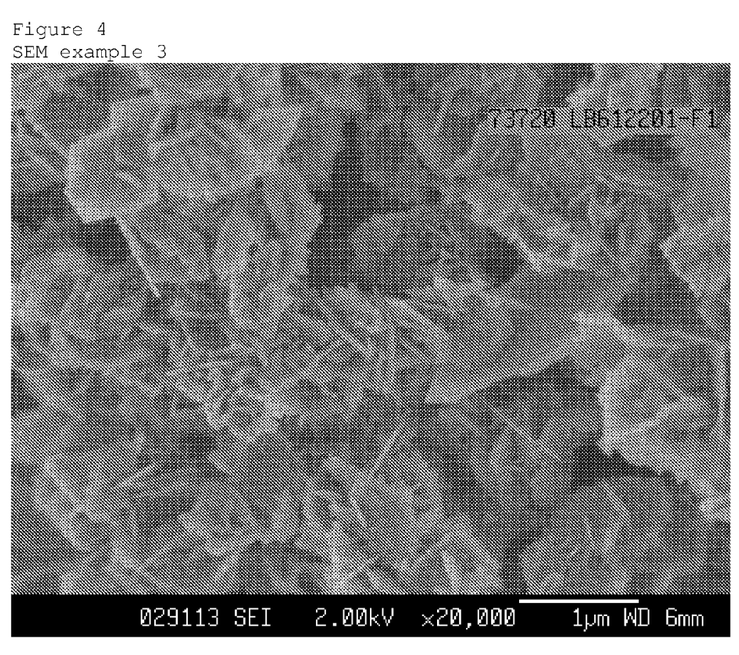
FIG. 4 is the Scan Electronic Microscopy of the dried as-synthesized solid product of Example 3.

This mixture was transferred to an autoclave and heated to 160° C. with a ramp rate of 25° C./hr, while stirring at 100 rpm. The crystallization was continued for 48 hrs at 160° C. After crystallization a solid product was recovered from the crystallization mixture, washed, and dried at 120° C. XRD analysis of the dried solid product showed it to be ZSM-57. The yield of the crystallization was 23.4 wt. %. The SEM of the dried solid product showed plate morphology (FIG. 4). Elemental analysis of the dried solid product showed a $Si/Al_2$ ratio of 44.4. The solid-content of the synthesis mixture was about 24.9 wt. %. The weight hourly throughput was 0.0045 $hr^{-1}$. The weight hourly throughput increased by about 580% in comparison with the reference example.

Example 4

A synthesis mixture was prepared by the procedure and raw materials used as the reference example, but with the following molar composition:

$$0.11Na_2O:0.018Al_2O_3:0.0246R_1:0.0246R_2:SiO_2:$$
$$10H_2O+2000 \text{ wtppm of LEV seeds}$$

Figure 5:
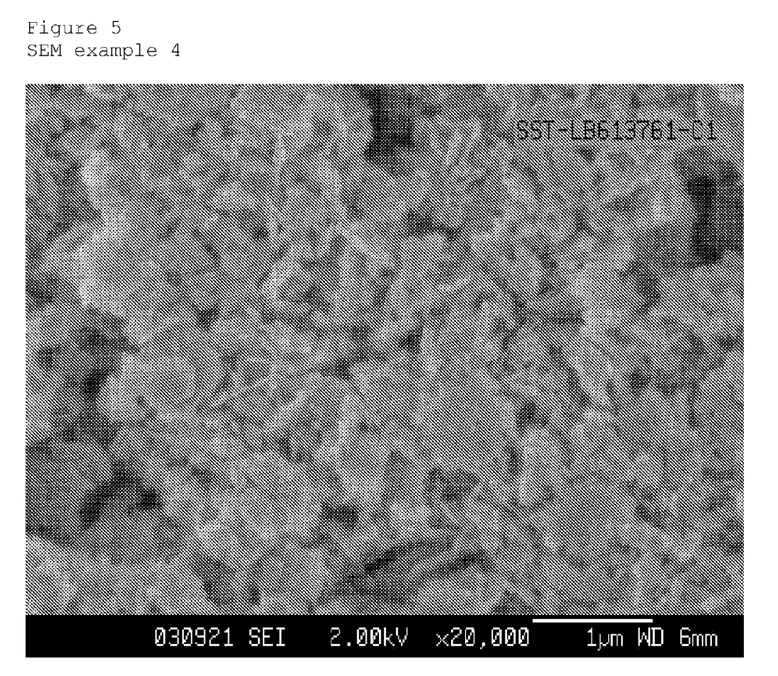
FIG. 5 is the Scan Electronic Microscopy of the dried as-synthesized solid product of Example 4.

This mixture was heated to 170° C. with a ramp rate of 25° C./hr, while stirring at 100 rpm. The reaction was continued for 36 hrs at 170° C. After crystallization the solid product was recovered from the reaction mixture, washed, and dried at 120° C. XRD analysis of the material showed it to be ZSM-57. The yield of the reaction was 18.7 wt. %. Elemental analysis of the dried solid product showed a $Si/Al_2$ ratio of 43.3. The solid-content of the synthesis mixture was about 23.4 wt. %. The weight hourly throughput was 0.0052 $hr^{-1}$. The SEM of the dried solid product showed plate morphology (FIG. 5). The weight hourly throughput increased by about 670% in comparison with the reference example.

Example 5

A synthesis mixture was prepared by the procedure and raw materials used as the reference example, but with the following molar composition:

$$0.11Na_2O:0.018Al_2O_3:0.0246R_1:0.0246R_2:SiO_2:$$
$$10H_2O+2000 \text{ wtppm of LEV seeds}$$

Figure 6:
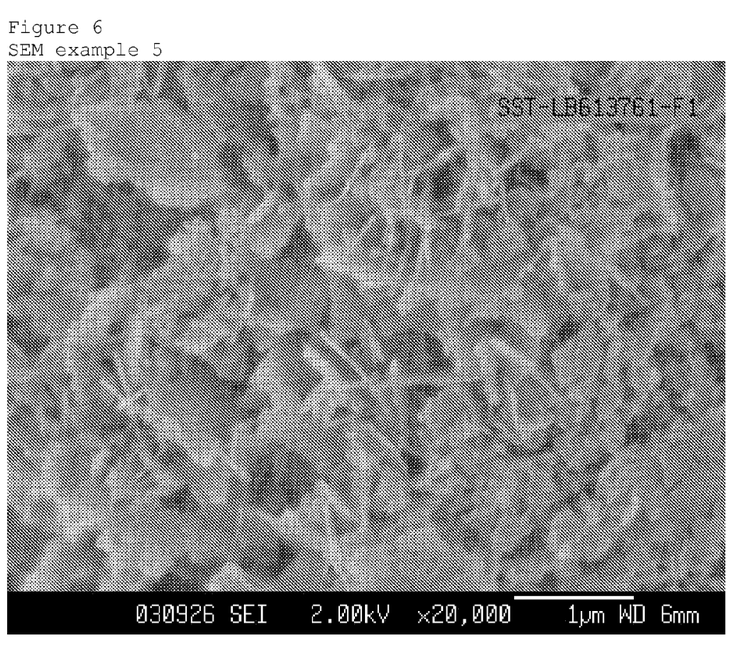
FIG. 6 is the Scan Electronic Microscopy of the dried as-synthesized solid product of Example 5.

This mixture was heated to 180° C. with a ramp rate of 25° C./hr, while stirring at 100 rpm. The reaction was continued for 24 hrs at 180° C. After crystallization the solid product was recovered from the reaction mixture, washed, and dried at 120° C. XRD analysis of the material showed it to be ZSM-57. The yield of the reaction was 20.8 wt. %. Elemental analysis of the dried solid product showed a Si/Al$_2$ ratio of 44.7. The solid-content of the synthesis mixture was about 23.4 wt. %. The weight hourly throughput was 0.0087 hr$^{-1}$. The SEM of the dried solid product showed plate morphology (FIG. 6). The weight hourly throughput increased by about 1100% in comparison with the reference example.

Example 6

The materials of examples 1, 2, 3, 4, 5 and the reference example were ion-exchanged with NH$_4$Cl according to the following procedure. Two gram material of any one of the examples 1, 2, 3, 4, 5 and the reference example was brought in 200 ml 0.5 N NH$_4$Cl. The mixture was heated to about 100° C. and hold under reflux overnight. After cooling, the mixture was washed on a filter with distilled water until the wash water was substantially chloride free. The catalyst was dried at 120° C. overnight followed by calcination in air at 510° C. for 16 hours. The powders were pelletized, i.e., crushed and sieved to 300-600 microns.

A catalyst was made by diluting 0.25 g pellets with 29.75 g SiC (0.5 mm) The catalyst was then loaded in a reactor for butene oligomerization test. The testing conditions were: a feed rate of 25 g/hr using a feed composed of 65 wt. % butene-1, 10 wt. % isobutane and 25 wt. % n-butane; a temperature of 195° C., and a pressure of 101 kPa-a. The heating was done electrically controlled by a thermocouple in the heating jacket around the reactor. The reaction temperature was measured via two thermocouples in the reactor. The conversion of the butene in weight percentage (wt. %) was measured by a HP5890 GC equipped with a HP-1 (30 meter) and a HP-AUS (50 meter) column. The selectivity to eight-carbon hydrocarbons (C$_8$) was measured by dividing the weight of the C$_8$ product with the weight of the butene converted. The deactivation of the catalyst was measured at a given temperature. The catalyst life was measured by the total weight of the butene converted (before regeneration of the catalyst) per unit weight of the catalyst.

Figure 7:
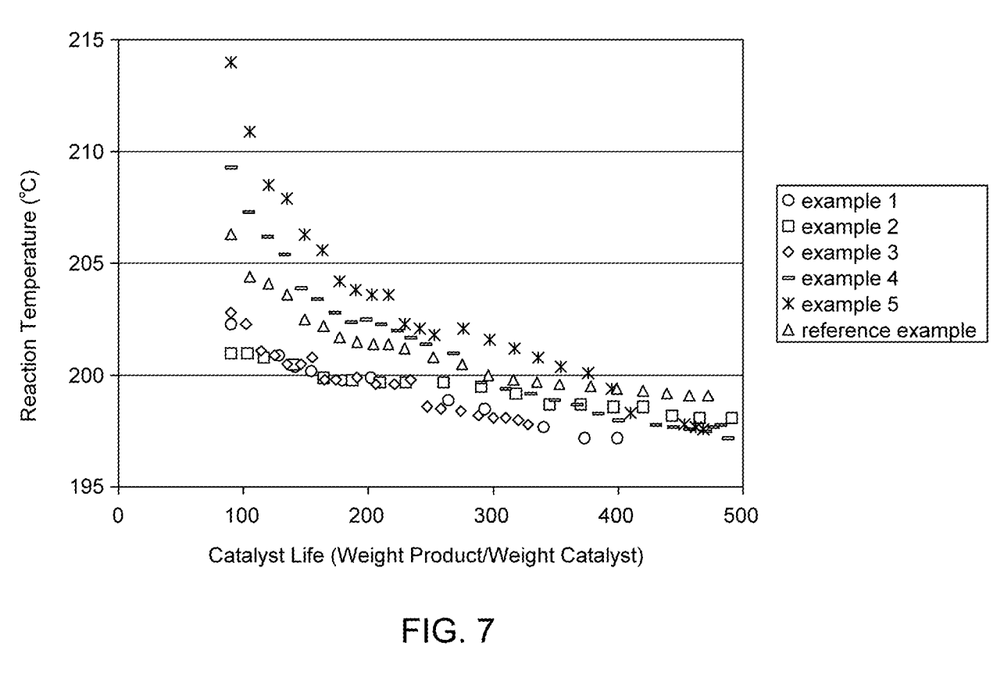
FIG. 7 is a plot of the reaction temperature versus the catalyst life for the ZSM-57 product of Examples 1, 2, 3, 4, 5, and Reference Example as tested in Example 6.
Figure 8:
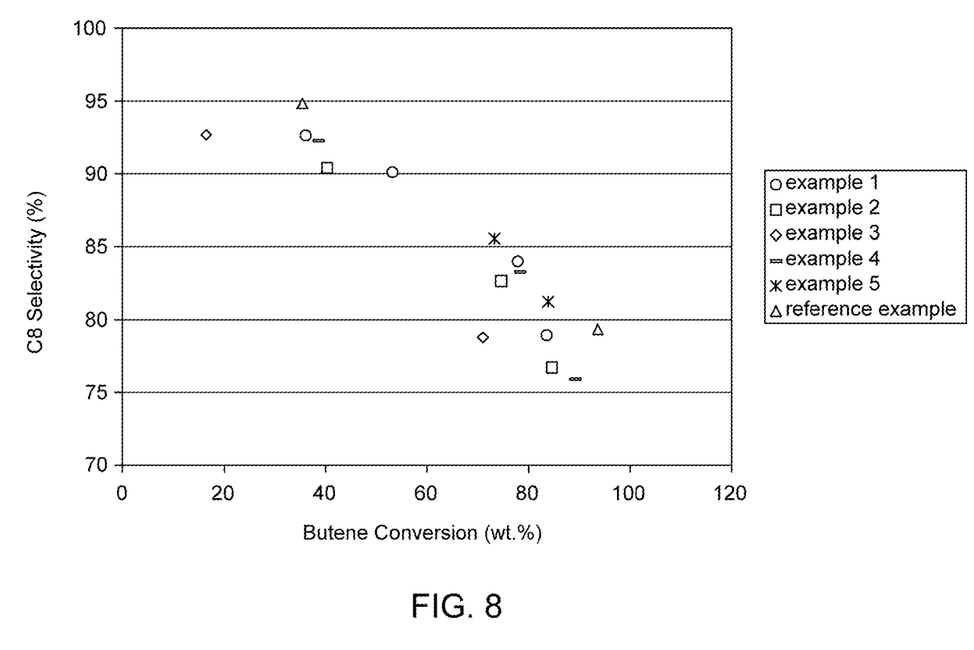
FIG. 8 is a plot of the $C_8$ selectivity versus the conversion of butenes for the ZSM-57 product of Examples 1, 2, 3, 4, 5, and reference example as tested in Example 6.

FIG. 7 showed the temperature of the reaction versus the catalyst life for all catalysts made from the materials of examples 1, 2, 3, 4, 5 and the reference example. FIG. 8 showed the selectivity to the C$_8$ versus the conversion of the butene for all catalysts made from the materials of examples 1, 2, 3, 4, 5 and the reference example. The materials of examples 1, 2, 3, 4, 5 and the reference example showed similar activity, selectivity, and catalyst life for the butene oligomerization reaction.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for hydrocarbon conversion comprising the steps of:
   (a) providing a mixture comprising at least one source of ions of tetravalent element (Y), at least one source of ions of trivalent element (X), at least one hydroxide source (OH—), at least one structure-directing-agent (R), at least one seed source (Seed), and water (H$_2$O), said mixture having the following mole composition (expressed in term of oxide):

YO$_2$:(n)X$_2$O$_3$:(x)OH—:(y)R:(z)H$_2$O+(m)Seed wherein m is in the range of from about 10 wtppm to about 2 wt. % (based on total weight of the synthesis mixture), n is in the range of from about 0.005 to 0.05, x is in the range of from about 0.01 to about 0.3, y is in the range of from about 0.03 to about 2; and z is in the range of from about 3 to about 8;
   (b) treating said mixture under crystallization conditions to form a product comprising said crystalline molecular sieve of MFS framework type and less than 50 wt. % of non-MFS material, based on the combination weight of non-MFS materials and the molecular sieve(s) of MFS framework type,
       wherein said structure-directing-agent R comprises N,N,N,N',N',N'-hexaethylpentane diammonium salt and a tetraethylammonium halide or hydroxide, said crystallization conditions comprise a temperature in the range of from about 150° C. to about 250° C., and a crystallization time less than 100 hr, and wherein the weight hourly throughput is at least 0.002 hr$^{-1}$;
   (c) recovering said crystalline molecular sieve of MFS framework type from said product; and,
   (d) contacting a hydrocarbon with said crystalline molecular sieve of MFS framework type under hydrocarbon conversion conditions to form a converted hydrocarbon.

2. The process recited in claim 1, wherein said tetravalent element is silicon.

3. The process recited in claim 1, wherein said trivalent element is aluminum.

4. The process recited in claim 1, wherein said seed is seed crystals of LEV framework type.

5. The process recited in claim 1, wherein said source of ions of tetravalent element is colloidal silica, said source of ions of trivalent element is aluminum sulphate and/or aluminum hydroxide, said hydroxide source is alkali metal hydroxide, and said seed source is LEV seeds.

6. The process recited in claim 1, wherein the halide is the bromide or chloride.

7. The process recited in claim 1, wherein said crystalline molecular sieve is ZSM-57.

8. The process recited in claim 1, wherein said crystallization conditions comprise a temperature in the range of from about 160° C. to about 200° C.

9. The process recited in claim 8, wherein said crystallization time is less than 72 hr.

10. The process recited in claim 1, wherein said m is from 10 to 2000 wtppm.

11. The process recited in claim 1, wherein said x is from 0.01 to 0.2.

12. The process recited in claim 1, wherein said y is from 0.035 to 0.2.

13. The process recited in claim 1, wherein said mixture has a solid-content of at least 15 wt. %.

* * * * *